(12) United States Patent
Boute et al.

(10) Patent No.: US 7,930,026 B2
(45) Date of Patent: Apr. 19, 2011

(54) MONITORING QRS COMPLEX TO IDENTIFY LEFT VENTRICULAR DYSFUNCTION

(75) Inventors: Willem Boute, Brummen (NL); Jos W Van Hove, Schiedam (NL)

(73) Assignee: Medtronic, Inc., Minneapolis, MN (US)

( * ) Notice: Subject to any disclaimer, the term of this patent is extended or adjusted under 35 U.S.C. 154(b) by 1782 days.

(21) Appl. No.: 10/424,555

(22) Filed: Apr. 25, 2003

(65) Prior Publication Data

US 2004/0215254 A1 Oct. 28, 2004

(51) Int. Cl.
*A61N 1/362* (2006.01)
(52) U.S. Cl. ............................ 607/9; 600/515
(58) Field of Classification Search .......... 607/14, 607/3, 9; 600/515
See application file for complete search history.

(56) References Cited

U.S. PATENT DOCUMENTS

| | | | |
|---|---|---|---|
| 4,305,396 A | 12/1981 | Wittkampf et al. | |
| 5,267,560 A | 12/1993 | Cohen | 607/25 |
| 5,331,966 A | 7/1994 | Bennett et al. | |
| 5,514,163 A | 5/1996 | Markowitz et al. | |
| 5,626,620 A | 5/1997 | Kieval et al. | |
| 5,674,254 A | 10/1997 | van Krieken | |
| 5,683,426 A | 11/1997 | Greenhut et al. | |
| 5,716,383 A | 2/1998 | Kieval et al. | |
| 5,836,987 A | 11/1998 | Baumann et al. | |
| 6,021,351 A | 2/2000 | Kadhiresan et al. | |
| 6,029,087 A | 2/2000 | Wohlgemuth | |
| 6,070,101 A | 5/2000 | Struble et al. | |
| 6,081,748 A | 6/2000 | Struble et al. | |
| 6,122,545 A | 9/2000 | Struble et al. | |
| 6,129,744 A * | 10/2000 | Boute | 607/25 |
| 6,512,952 B2 | 1/2003 | Stahmann et al. | |
| 2002/0077559 A1* | 6/2002 | Ding et al. | 600/509 |
| 2002/0082509 A1 | 6/2002 | Vanderlinde et al. | |

(Continued)

FOREIGN PATENT DOCUMENTS

EP 0 920 885 A1 6/1999

OTHER PUBLICATIONS

Murkofsky et al., "A Prolonged QRS Duration on Surface Electrocardiogram is a Specific Indicator of Left Ventricular Dysfunction," JACC, vol. 32, No. 2, Aug. 1998, pp. 476-482.

(Continued)

*Primary Examiner* — Niketa I Patel
*Assistant Examiner* — Alyssa M Alter
(74) *Attorney, Agent, or Firm* — Stephen W. Bauer; Reed A. Duthler

(57) ABSTRACT

An implantable medical device identifies onset and/or progression of left ventricular dysfunction (LVD). The implantable medical device receives a signal that represents electrical activity within a heart, e.g., an electrogram signal, and digitally processes the signal to assess left ventricular function. In particular, the implantable medical device measures at least one characteristic of QRS complexes within the signal, and assesses left ventricular function based on measurements. The implantable medical device may, for example, measure the width of the QRS complexes and/or the amplitude of the R-waves within the QRS complexes. The implantable medical device may alert a patient or clinician of the onset or progression of LVD, and may control delivery of therapies, such as rate-responsive pacing and cardiac resynchronization pacing, based on the measurements. The implantable medical device may also control delivery of a drug by an implanted drug delivery device, e.g., drug pump, based on the measurements.

27 Claims, 7 Drawing Sheets

U.S. PATENT DOCUMENTS

| | | | |
|---|---|---|---|
| 2002/0082654 A1 | 6/2002 | Kramer et al. | |
| 2002/0082656 A1 | 6/2002 | Stahmann et al. | |
| 2002/0082662 A1 | 6/2002 | Vanderlinde et al. | |
| 2002/0082663 A1 | 6/2002 | Stahmann et al. | |
| 2002/0161307 A1 | 10/2002 | Yu et al. | |
| 2002/0177880 A1 | 11/2002 | Fishler | |
| 2002/0193835 A1 | 12/2002 | Baker | |
| 2003/0004548 A1 | 1/2003 | Warkentin | |
| 2003/0014084 A1* | 1/2003 | VanHout | 607/9 |

OTHER PUBLICATIONS

Cazeau et al., "Effects of Multisite Biventricular Pacing in Patients with Heart Failure and Intraventricular Conduction Delay," New England Journal of Medicine, vol. 344, No. 12, Mar. 22, 2001, pp. 873-880.

Auricchio et al., "Does Fusion Contribute to the Improvement of LV Systolic Function of Heart Failure Patients When Pacing the LV with Varying AV Delays?" PACE, vol. 22, No. 4, Part II, May 1999, abstract #203.

Vogt et al., "Electrocardiographic Remodeling in Patients Paced for Heart Failure," The American Journal of Cardiology, vol. 86 (9A), Nov. 2000, pp. 152K-156K.

Butter et al., "Should Stimulation Site Be Tailored in the Individual Heart Failure Patient?" The American Journal of Cardiology, vol. 86 (9A), Nov. 2000, pp. 144K-151K.

Brouwer et al., "Analysis of Atrial Sensed Far-Field Ventricular Signals: A Reassessment," PACE, vol. 20, Part I, Apr. 1997, pp. 916-922.

* cited by examiner

MONITORING QRS COMPLEX TO IDENTIFY LEFT VENTRICULAR DYSFUNCTION

FIELD OF THE INVENTION

The invention relates to medical devices and, more particularly, to implantable medical devices used for monitoring cardiac function.

BACKGROUND OF THE INVENTION

Left ventricular dysfunction (LVD) is a symptom of a variety of cardiac disorders. For example, LVD may be caused by dilated cardiomyopathy or ischemia. LVD may also be caused by left bundle branch block (LBBB), which is a conduction disorder that may cause ventricular dysynchrony.

In any particular patient, a single cardiac disorder may cause LVD. However, such disorders often have complicated cause-and-effect interrelationships, and LVD in any particular patient is most often caused by the progression of two or more such disorders. Moreover, some disorders, such as dilated cardiomyopathy, become progressively worse in an attempt to overcome LVD, which ultimately leads to even more severe LVD.

LVD refers to the ineffectiveness of a heart, and more particularly the left ventricle of the heart, as a pump for blood. Patients with LVD may experience fatigue, dizziness, disorientation, edema, shortness-of-breath, end-organ failure, and a host of other symptoms associated with insufficient cardiac output and congestive heart failure. Patients with diagnosed LVD may be treated with drugs, such as beta-blockers, ACE inhibitors, or inotropic drugs. Beta-blockers and ACE inhibitors increase the effectiveness of the left ventricle by decreasing the resistance faced by the left ventricle, and inotropic drugs increase the effectiveness of the left ventricle by increasing the contractility of the heart. In some cases, patients with diagnosed LVD may receive a pacemaker that paces the heart in a way that resynchronizes ventricular contractions and increases the effectiveness of the left ventricle.

Although LVD could be defined in terms of cardiac output, i.e., the volume of blood pumped by a heart per minute, LVD is generally diagnosed when the left ventricular ejection fraction (LVEF) falls below a threshold, e.g., 0.40. In any event, both cardiac output and LVEF must generally be measured in a clinical setting, and tests to assess cardiac output and LVEF are generally not performed unless the patient is symptomatic. LVD can progress from onset to a life-threatening condition quite rapidly. Thus, LVD is frequently not detected and diagnosed until a patient experiences symptoms sufficient to cause hospitalization, at which time the disorders underlying the LVD may have already progressed substantially.

BRIEF SUMMARY OF THE INVENTION

The invention is directed to techniques for cardiac monitoring. In particular, an implantable medical device identifies onset and/or progression of left ventricular dysfunction (LVD). The implantable medical device receives a signal that represents electrical activity within a heart, e.g., an electrogram signal, and digitally processes the signal to assess left ventricular function. The implantable medical device may allow onset or progression of LVD to be detected more quickly and outside of a clinical setting In particular, the implantable medical device measures at least one characteristic of QRS complexes within the signal, and assesses left ventricular function based on the measurement. The implantable medical device may, for example, measure the width of the QRS complexes and/or the amplitude of the R-waves within the QRS complexes. Increased QRS complex width and decreased R-wave amplitude may indicate onset or progression of LVD, and particularly LVD associated with ventricular dysynchrony.

The implantable medical device may alert a patient or clinician of the onset or progression of LVD, and may control delivery of therapies, such as rate-responsive pacing and cardiac resynchronization pacing, based on the measurements. The implantable medical device may also control delivery of a drug by an implanted drug delivery device, e.g., drug pump, based on the measurements. The implantable medical device may detect onset or progression of LVD based on trends in the measurements over time, and thus avoid indicating LVD or making therapy adjustments based on cyclical or non-LVD related variations in the measurements.

In one embodiment, the invention provides a device that includes electrodes implanted within a patient and a processor. The electrodes detect a signal that represents electrical activity within a heart. The processor digitally processes the signal to measure a value of a characteristic of QRS complexes for each of a plurality of QRS complexes within the digital signal, and indicates left ventricular dysfunction to a user based on the measured values for the QRS complexes. The processor may comprise a digital signal processor to digitally process the digital signal, and a microprocessor to indicate ventricular dysfunction to a user based on the measured values. The measured characteristic of the QRS complexes may, for example, be QRS width or R-wave amplitude.

In another embodiment, the invention is directed to a method for assessing cardiac function in which a signal that represents electrical activity within a heart is received via electrodes implanted within a patient. The signal is digitally processed to measure a value of a characteristic of QRS complexes for each of a plurality of QRS complexes within the signal. Left ventricular dysfunction is indicated to a user based on the measured values for the QRS complexes.

In another embodiment, the invention is directed to a method in which a signal that represents electrical activity within a heart is received via electrodes implanted within a patient. The signal is digitally processed to measure a width for each of a plurality of QRS complexes within the signal and an amplitude for each R-wave within the plurality of QRS complexes, and left ventricular dysfunction is indicated to a user based on the measured QRS widths and R-wave amplitudes.

In an additional embodiment, the invention provides a system that includes a monitoring device and a drug delivery device. The monitoring device digitally processes a signal that represents electrical activity within a heart to measure a value of a characteristic of QRS complexes for each of a plurality of QRS complexes within the signal, and indicates left ventricular dysfunction based on the measured values. The drug delivery device delivers a drug to the patient based on the indication.

DETAILED DESCRIPTION OF THE INVENTION

Figure 1:
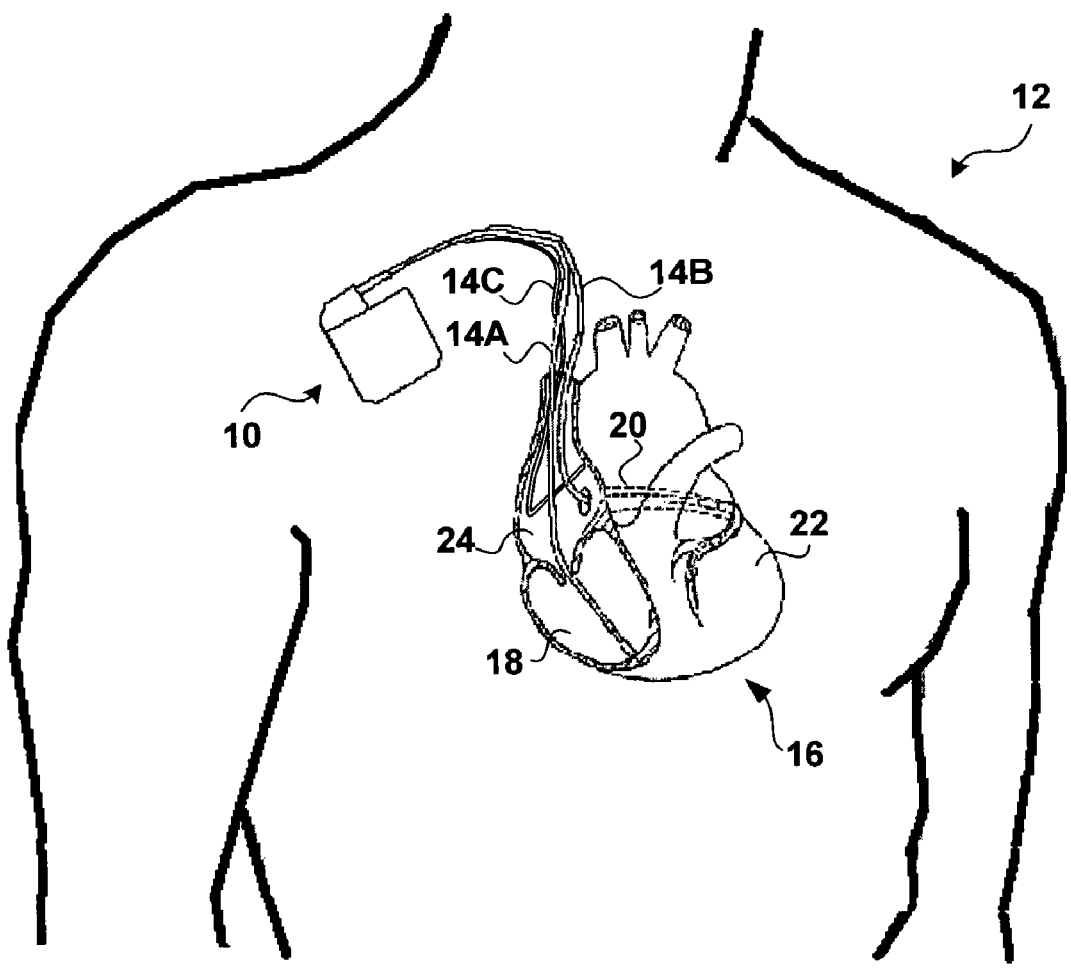
FIG. 1 is a conceptual diagram illustrating an exemplary implantable medical device implanted in a patient.

FIG. 1 is a conceptual diagram illustrating an exemplary implantable medical device (IMD) 10 implanted in a patient 12. IMD 10 may, as shown in FIG. 1, take the form of a multi-chamber cardiac pacemaker. In the exemplary embodiment illustrated in FIG. 1, IMD 10 is coupled to leads 14A, 14B and 14C (collectively "leads 14") that extend into the heart 16 of patient 12.

More particularly, right ventricular (RV) lead 14A may extend through one or more veins (not shown), the superior vena cava (not shown), and right atrium 24, and into right ventricle 18. Left ventricular (LV) coronary sinus lead 14B may extend through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

IMD 10 may sense electrical signals attendant to the depolarization and repolarization of heart 16 via electrodes (not shown) located on leads 14. In some embodiments, IMD 10 may also provide pacing, cardioversion, or defibrillation pulses via electrodes located on leads 14. The electrodes located on leads 14 may be unipolar or bipolar, as is well known in the art.

As will be described in greater detail below, IMD 10 receives a signal that represents electrical activity within heart 16, and digitally processes the signal to assess left ventricular function. In particular, IMD 10 measures at least one characteristic of QRS complexes within the signal and assesses left ventricular function based on the measurements. IMD 10 may, for example, measure the width of the QRS complexes and/or the amplitude of the R-waves within the QRS complexes.

IMD 10 may identify onset or progression of left ventricular dysfunction (LVD). In general, QRS widths over 150 ms and R-wave amplitudes less than 0.4 mV are indicative of LVD. Increased QRS widths and decreased R-wave amplitudes are especially indicative of ventricular dysynchrony associated with LVD. As will be described below, IMD 10 may identify LVD based on increased QRS width or decreased R-wave amplitude over time. In some embodiments, IMD 10 may identify LVD based on a combination of both increased QRS width and decreased R-wave amplitude for increased selectivity.

As will be described in greater detail below, IMD 10 may indicate onset or progression of LVD to a user, such as patient 12 or a clinician (not shown). IMD 10 may also control delivery of therapy to patient 12, e.g., initiate or modify therapy, based on the assessment of left ventricular function, as will be described in greater detail below.

IMD 10 may be capable of detecting onset of LVD, and may allow LVD to be detected outside of a clinic setting. In other words, IMD 10 may enable early LVD detection which may not otherwise be possible. In some embodiments, IMD 10 may alert patient 12 of a problem, i.e., identification of LVD, via a patient alarm, which would cause patient 12 to contact a clinician who could diagnose LVD.

IMD 10 may be implanted in patient 12 for reasons other than detection of LVD. For example, IMD 10 may be implanted in patient 12 to provide rate-responsive pacing therapy or defibrillation therapy. Patients who receive IMDs to provide such therapies may be more likely than the general public to develop LVD. Therefore, IMD 10 may assess left ventricular function in addition to providing such therapies, allowing onset of LVD to be detected in an "at risk" patient 12.

The configuration of IMD 10 and leads 14 illustrated in FIG. 1 is merely exemplary. IMD 10 may be coupled any number of leads 14 that extend to a variety of positions within or outside of heart 16. For example, at least some of leads 14 may be epicardial leads.

Moreover, IMD 10 need not be coupled to any leads 14 at all, but may instead receive a signal that represents electrical activity within heart 16 via electrodes integral with a housing of IMD 10 (not shown). IMD 10 may, for example, take the form of an implantable loop recorder. Further, IMD 10 need not be implanted within patient 12, but may instead be coupled with subcutaneous leads 14 that extend through the skin of patient 12 to a variety of positions within or outside of heart 16.

Figure 2:
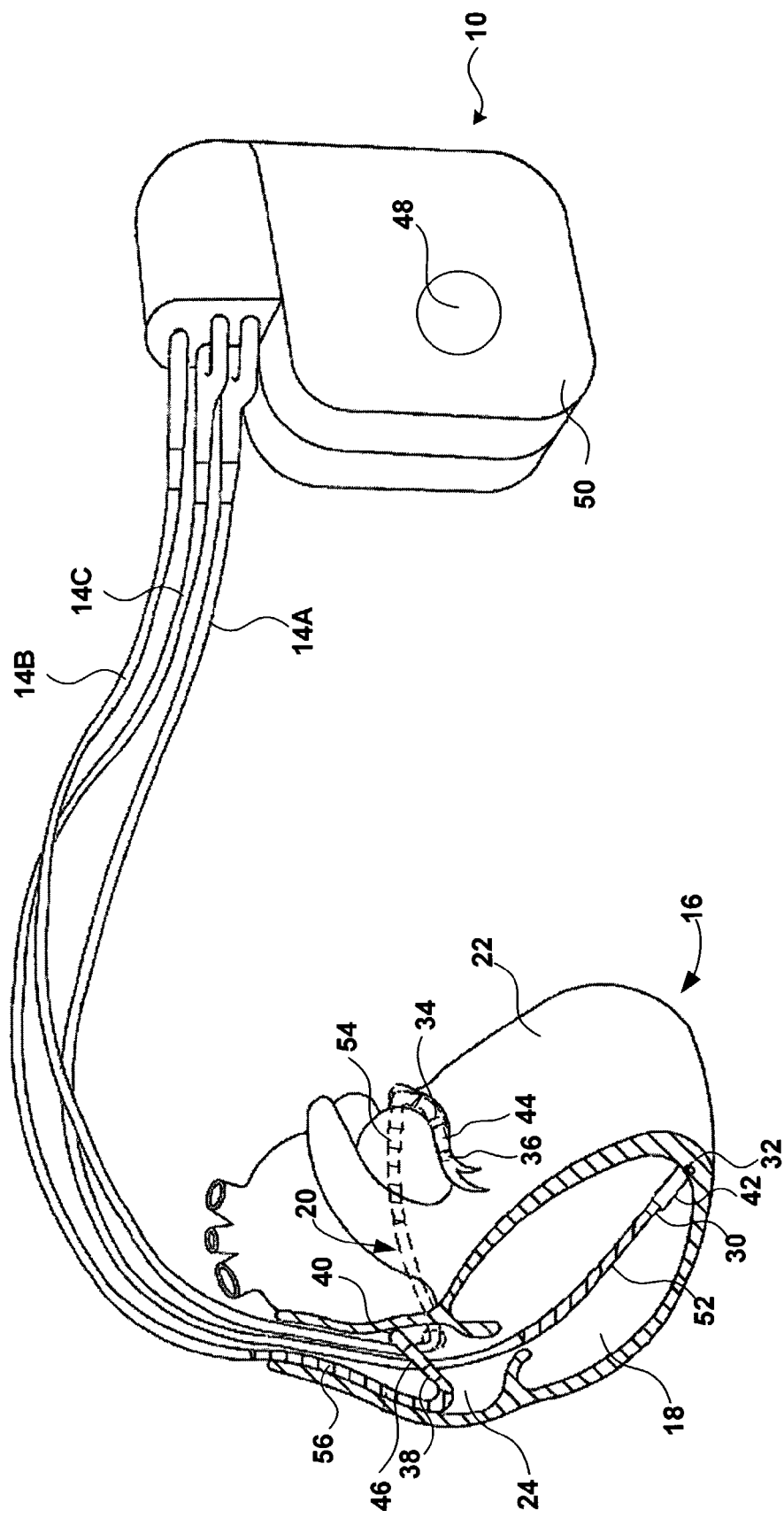
FIG. 2 is conceptual diagram further illustrating the implantable medical device of FIG. 1 and the heart of the patient.

FIG. 2 is conceptual diagram further illustrating IMD 10 and heart 16 of patient 12. Each of leads 14 may include an elongated insulative lead body carrying a number of concentric coiled conductors separated from one another by tubular insulative sheaths. Located adjacent distal end of leads 14A, 14B and 14C are bipolar electrodes 30 and 32, 34 and 36, and 38 and 40 respectively. Electrodes 30, 34 and 38 may take the form of ring electrodes, and electrodes 32, 36 and 40 may take the form of extendable helix tip electrodes mounted retractably within insulative electrode heads 42, 44 and 46, respectively. Each of the electrodes 30-40 is coupled to one of the coiled conductors within the lead body of its associated lead 14.

Sense/pace electrodes 30, 32, 34, 36, 38 and 40 sense electrical signals attendant to the depolarization and repolarization of heart 16. The electrical signals are conducted to IMD 10 via leads 14. Sense/pace electrodes 30, 32, 34, 36, 38 and 40 further may deliver pacing to cause depolarization of cardiac tissue in the vicinity thereof. IMD 10 may also include one or more indifferent housing electrodes, such as housing electrode 48, formed integral with an outer surface of the hermetically sealed housing 50 of IMD 10. Any of electrodes 30, 32, 34, 36, 38 and 40 may be used for unipolar sensing or pacing in combination with housing electrode 48.

Leads 14A, 14B and 14C may also, as shown in FIG. 2, include elongated coil electrodes 52, 54 and 56, respectively. IMD 10 may deliver defibrillation or cardioversion shocks to heart 16 via defibrillation electrodes 52-56. Defibrillation electrodes 52-56 may be fabricated from platinum, platinum alloy or other materials known to be usable in implantable defibrillation electrodes, and may be about 5 cm in length.

Figure 3:
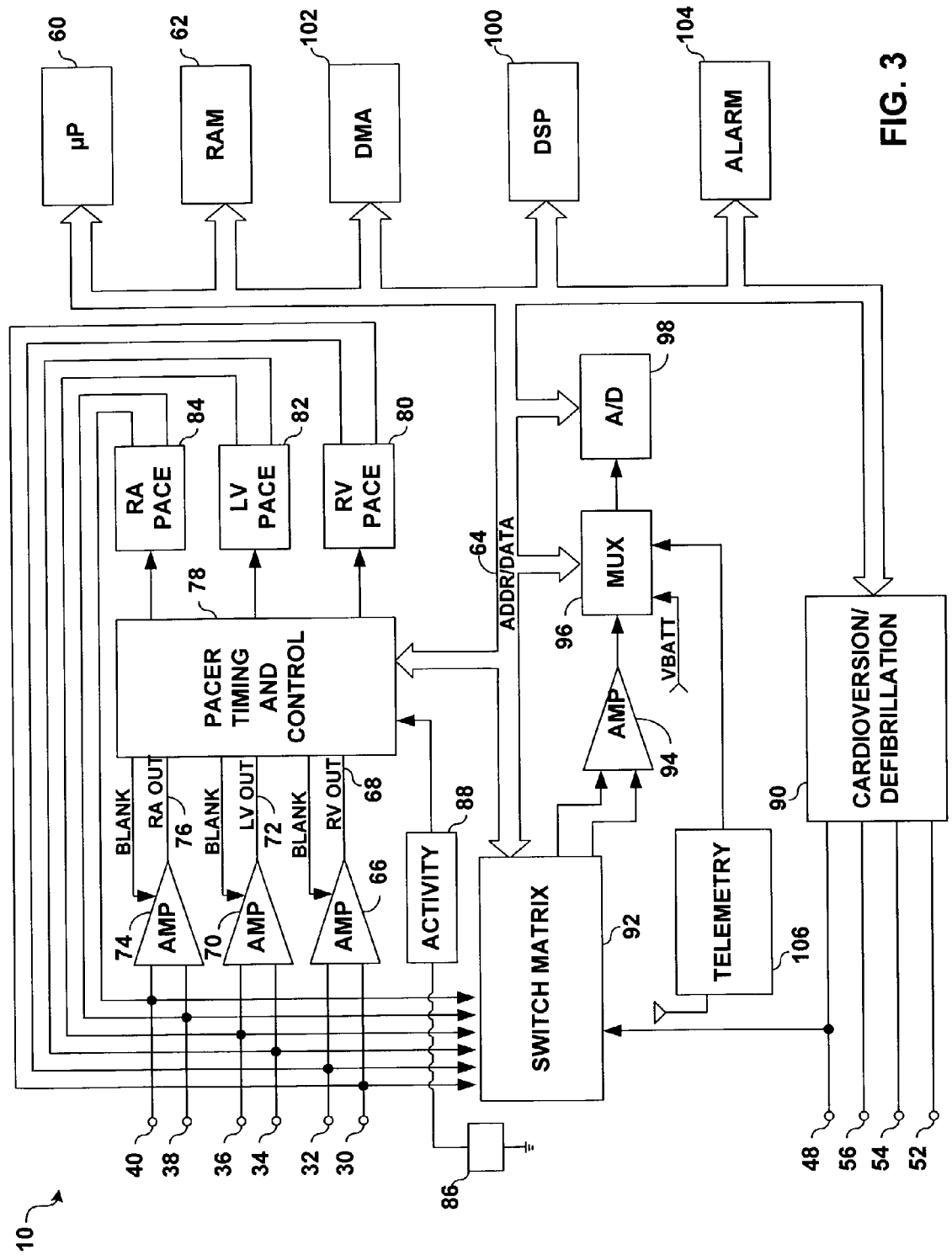
FIG. 3 is a functional block diagram of the implantable medical device of FIG. 1.

FIG. 3 is a functional block diagram of IMD 10. As shown in FIG. 3, IMD 10 may take the form of a multi-chamber pacemaker-cardioverter-defibrillator (PCD) having a microprocessor-based architecture. However, this diagram should be taken as exemplary of the type of device in which various embodiments of the present invention may be embodied, and not as limiting, as it is believed that the invention may be practiced in a wide variety of device implementations, including devices that provide pacing therapies but do not provide cardioverter and/or defibrillator functionality, and devices that provide no therapy at all, such as an implantable loop recorder.

IMD 10 includes a microprocessor 60. Microprocessor 60 may execute program instructions stored in memory, such as a ROM (not shown), EEPROM (not shown), and/or RAM 62, which control microprocessor 60 to perform the functions ascribed to microprocessor 60 herein. Microprocessor 60 may be coupled to, e.g., communication with and/or control, various other components of IMD 10 via an address/data bus 64.

Electrodes 30 and 32 are coupled to amplifier 66, which may take the form of an automatic gain controlled amplifier providing an adjustable sensing threshold as a function of the measured R-wave amplitude. A signal is generated on RV out line 68 whenever the signal sensed between electrodes 30 and 32 exceeds the present sensing threshold. Electrodes 34 and 36 are coupled to amplifier 70, which also may take the form of an automatic gain controlled amplifier providing an adjustable sensing threshold as a function of measured R-wave amplitude. A signal is generated on LV out line 72 whenever the signal sensed between electrodes 34 and 36 exceeds the present sensing threshold. Electrodes 38 and 40 are coupled to amplifier 74, which may take the form of an automatic gain controlled amplifier providing an adjustable sensing threshold as a function of the measured P-wave amplitude. A signal is generated on RA out line 76 whenever the signal between electrodes 38 and 40 exceeds the present sensing threshold.

IMD 10 may pace heart 16. Pacer timing/control circuitry 78 preferably includes programmable digital counters which control the basic time intervals associated with modes of pacing. Circuitry 78 also preferably controls escape intervals associated with pacing. In the exemplary bi-ventricular pacing environment, pacer timing/control circuitry 78 controls the ventricular escape interval that is used to time pacing pulses delivered to the ventricles, and, where cardiac resynchronization pacing is provided, may control an interval between delivery of pulses to the ventricles 18,22.

Intervals defined by pacing circuitry 78 may also include atrial pacing escape intervals, and the refractory periods during which sensed R-waves and P-waves are ineffective to restart timing of the escape intervals and the pulse widths of the pacing pulses. The durations of these intervals are determined by microprocessor 60 in response to data stored in RAM 62, and are communicated to circuitry 78 via address/data bus 64. Pacer timing/control circuitry 78 also determines the amplitude of the cardiac pacing pulses under control of microprocessor 60.

Microprocessor 60 may operate as an interrupt driven device, and is responsive to interrupts from pacer timing/control circuitry 78 corresponding to the occurrence of sensed R-waves and corresponding to the generation of cardiac pacing pulses. Those interrupts are provided via data/address bus 66. Any necessary mathematical calculations to be performed by microprocessor 60 and any updating of the values or intervals controlled by pacer timing/control circuitry 78 take place following such interrupts.

During pacing, escape interval counters within pacer timing/control circuitry 78 may be reset upon sensing of R-waves and P-waves as indicated by signals on lines 68, 72 and 76. In accordance with the selected mode of pacing, pacer timing/control circuitry 78 triggers generation of pacing pulses by one or more of pacer output circuits 80, 82 and 84, which are coupled to electrodes 30 and 32, 34 and 36, and 38 and 40, respectively. Output circuits 80, 82 and 84 may be pulse generation circuits known in the art, which include capacitors and switches for the storage and delivery of energy as a pulse.

Pacer timing/control circuitry 78 resets escape interval counters upon detection of R-waves or P-waves, or generation of pacing pulses, and thereby control the basic timing of cardiac pacing functions.

IMD 10 may provide rate-responsive pacing therapy to patient 12. IMD 10 is shown in FIG. 3 as including an activity sensor 86. Activity sensor 86 typically (although not necessarily) provides a sensor output that varies as a function of a measured parameter relating to metabolic requirements of patient 12. Activity sensor 86 may, for example, be a piezoceramic accelerometer bonded to a hybrid circuit located inside housing 50 (shown in FIGS. 1 and 2), or electrodes to detect respiration rate of patient 12 via cyclical variations in the thoracic impedance of patient 12. Microprocessor 60 may also measure activity based on the length of detected QT intervals within electrical signals received from combinations of electrodes 30-36 and 48, which vary based on activity, and in effect act as an activity sensor.

The output signal provided by activity sensor 86 is coupled to an activity detection circuit 88, which determines the activity level, e.g., counts, of patient 12 based on the output. The activity level or counts are provided to pacer timing/control circuit 78, which adjusts one or more escape intervals based on the activity level or counts and parameters or functions provided by microprocessor 60 to provide rate-responsive pacing. IMD 10 may include multiple activity sensors 86 and may provide rate-responsive pacing based on a combination or blending of the outputs of the various sensors.

IMD 10 may detect ventricular and/or atrial tachycardias or fibrillations of heart 16 using tachycardia and fibrillation detection techniques and algorithms known in the art. For example, the presence of a ventricular or atrial tachycardia or fibrillation may be confirmed by detecting a sustained series of short R-R or P-P intervals of an average rate indicative of tachycardia, or an unbroken series of short R-R or P-P intervals. IMD 10 is also capable of delivering one or more antitachycardia pacing (ATP) therapies to heart 16, and cardioversion and/or defibrillation pulses to heart 16 via one or more of electrodes 48, 52, 54 and 56.

Electrodes 48, 52, 54 and 56, are coupled to a cardioversion/defibrillation circuit 90, which delivers cardioversion and defibrillation pulses under the control of microprocessor 60. Circuit 90 may include energy storage circuits such as capacitors, switches for coupling the storage circuits to electrodes 48, 52, 54 and 5, and logic for controlling the coupling of the storage circuits to the electrodes to create pulses with desired polarities and shapes. Microprocessor 60 may employ an escape interval counter to control timing of such cardioversion and defibrillation pulses, as well as associated refractory periods.

As mentioned above, IMD 10 receives a signal that represents electrical activity within heart 16, digitally processes the signal to measure at least one characteristic of QRS complexes within the signal, and assesses left ventricular function based on measurements. Switch matrix 92 is used to select which of the available electrodes 30-40 and 48 are coupled to wide band (0.5-200 Hz) amplifier 94 for use in digital signal analysis. As will be described in greater detail below, any of a number of potential combinations of these electrodes may be used, so long as the signal provided by the combination allows for identification and measurement of characteristics of QRS complexes. Selection of electrodes is controlled by microprocessor 60 via data/address bus 66, and the selections may be varied as desired.

The analog signal derived from the selected electrodes and amplified by amplifier 94 is provided to multiplexer 96, and thereafter converted to a multi-bit digital signal by A/D converter 98. A digital signal processor (DSP) 100 may process the multi-bit digital signal to measure QRS widths and/or R-wave amplitudes, as will be described in greater detail below. In some embodiments, the digital signal may be stored in RAM 62 under control of direct memory access circuit 102 for later analysis by DSP 100. Although IMD 10 is described herein as having separate processors, microprocessor 60 may perform both the functions ascribed to it herein and digital signal analysis functions ascribed to DSP 100 herein. Moreover, although described herein in the context of microprocessor based PCD embodiment IMD 10, the invention may be embodied in various implantable medical devices that include one or more processors, which may be microprocessors, DSPs, FPGAs, or other digital logic circuits.

The QRS widths and/or R-wave amplitudes measured by DSP 100 may be stored in RAM 62 where they may be retrieved for analysis by microprocessor 60. Based on the analysis of the widths and/or amplitudes, which will be described in greater detail below, microprocessor 60 may identify onset or progression of LVD. Based on the identification, microprocessor 60 may provide an indication of LVD onset or progression to a user, such as patient 12 or a clinician. For example, IMD 10 may include an alarm 104 that provides an audible signal to patient 12 in whom IMD 10 is implanted. Microprocessor 60 may activate alarm 104 in response to identification of onset or progression of LVD to alert patient 12 to a possible problem that may require consultation with a clinician.

As another example, IMD 10 may be programmable by means of an external programming unit (not shown), and certain features of IMD 10 may be controlled by a patient activator (not shown). Both the programming unit and the patient activator communicate with IMD 10 via telemetry circuit 106 using RF telemetry techniques known in the art. Microprocessor 60 may store an indication of onset or progression of LVD in RAM 62, and provide the indication to either patient 12 or a clinician when interrogated by a patient activator or programmer.

Microprocessor 60 may also control delivery of therapies to patient 12 based on the measured QRS widths and R-wave amplitudes. For example, microprocessor 60 may control pacer timing/control circuit 78 to adjust escape intervals to decrease an amount of right ventricular pacing, which can contribute to LVD. Microprocessor 60 may provide circuit 78 with new rate-response parameters or functions that decrease the aggressiveness of rate-responsive pacing, or to change the relative contribution of different sensor outputs to the determination of the overall rate-response. Microprocessor 60 may initiate or modify cardiac resynchronization pacing by providing circuit 78 with or altering a V-V offset interval to cause circuit 78 to control delivery of pulses to the right and left ventricles 18,22 at offset times. Microprocessor 60 may also control an implanted drug delivery device to deliver or to change the rate of delivery of drugs, such as beta-blockers, ACE inhibitors, or inotropic drugs, which are used to treat LVD.

Figure 4:
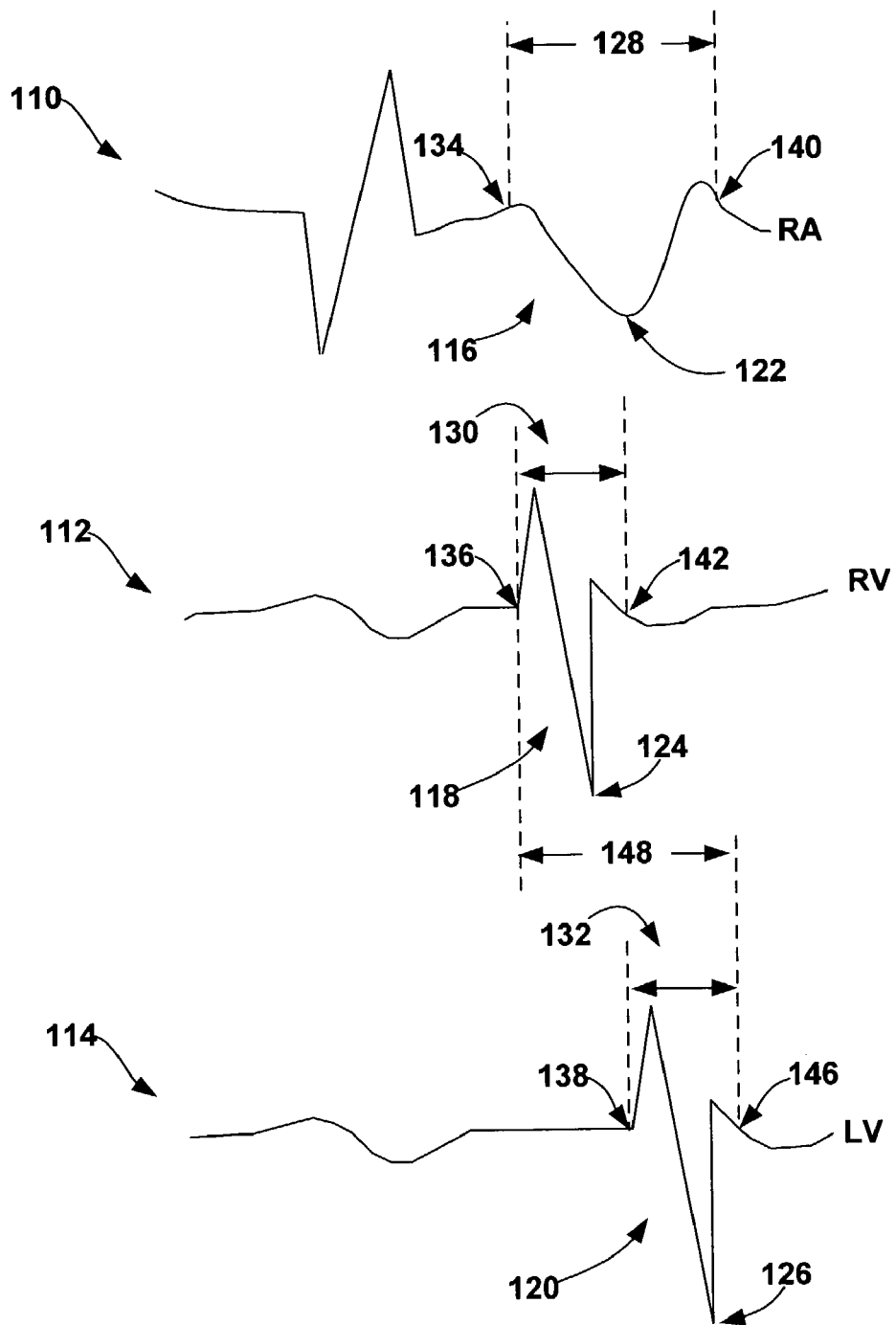
FIG. 4 is a timing diagram illustrating example electrogram signals that may be processed by the implantable medical device of FIG. 1 to identify left ventricular dysfunction.

FIG. 4 is a timing diagram illustrating example analog electrogram (EGM) signals that may be digitally processed by IMD 10 to identify onset or progression of LVD. Signal 110 is a right atrial EGM. Signal 10 may be detected using electrodes 38 and 40 of RA lead 14C in a bipolar configuration, or one of electrodes 38 and 40 and housing electrode 48 in a unipolar configuration. Signals 112 and 114 are right and left ventricular EGMs, respectively, and may be detected via RV lead 14C and LV coronary sinus lead 14B, respectively. Signals 112 and 114 may be detected using bipolar electrode pairs 30, 32 and 34, 36, or one electrode from each pair and housing electrode 48 in a unipolar configuration.

In general, it is preferred that IMD 10 digitally process signals that include far-field QRS complexes, such as right atrial EGM 110, or signals 112 and 114 detected via ventricles 18, 22 using a unipolar electrode configuration. Processing these signals is preferred because such signals include QRS complexes that are more "global" in that they reflect depolarization of both ventricles 18, 22, and thus more accurately reflect overall ventricular function. Moreover, such "global" signals allow IMD 10 to detect LVD resulting from ventricular dyssynchrony caused by a conduction disorder, such as a left bundle branch block (LBBB). In addition to atrial EGM signal 112, IMD 10 may detect signals that include far-field QRS complexes using two or more housing electrodes 48. Detecting cardiac signals via housing electrodes 48 may enable embodiments of IMD 10 that do not include leads, such as implantable loop recorder embodiments of IMD 10.

Signals 110-114 include QRS complexes 116, 118 and 120, respectively. QRS complexes 116-120 include R-waves 122, 124 and 126, respectively. IMD 10 may digitally process one or more of analog EGM signals 110-114 to measure one or more of QRS widths 128, 130 and 132, and/or amplitudes of R-waves 122-126. More particularly, A/D converter 98 of IMD 10 may convert one or more of EGM signals 110-114 to digital signals. DSP 100 of IMD 10 digitally processes the digital signals to measure QRS widths and/or R-wave amplitudes. For ease of illustration, only a portion of each of EGM signals 110-114 representing a single cardiac cycle of heart 16 is shown in FIG. 4. However, it is understood that DSP 100 measures multiple QRS widths and/or R-wave amplitudes within each of the one or more signals 110-114 digitally processed. DSP 100 provides microprocessor 60 with the measured values as described above. Where two or more signals are processed, DSP 100 or microprocessor 60 may determine average values or weighted average values for each cardiac cycle based on the values for each signal.

In order to measure these characteristics of QRS complexes 116-120, DSP 100 first identifies QRS complexes 116-120 within signals 110-114. DSP 100 may identify QRS complexes within signals 110-114 by any methods known in the art. For example, DSP 100 may receive indications of the occurrence of R-waves from pacer timing/control circuit 78, and identify QRS complexes based on these indications. As another example, DSP 100 may identify QRS complexes by detecting a number of threshold-crossings of the digital signal or zero-crossings of the first derivative of the signal occurring within a time window. As yet another example, DSP 100 may detect QRS complexes within signals 110-114 using techniques described in commonly assigned U.S. Pat. No. 6,029,087, to Wohlgemuth, and titled "Cardiac Pacing System With Improved Physiological Event Classification Based on DSP."

DSP 100 may measure widths 128-132 as periods of time from beginning points 134, 136 and 138 to ending points 140, 142 and 144 of QRS complexes 116-120, respectively. Where RV EGM 112 and LV EGM 114 are bipolar ventricular EGMs, DSP may still measure a "global" QRS width 148 by measuring from the first beginning point to the last ending point of QRS complexes 118 and 120, e.g., beginning point 136 of QRS complex 118 to ending point 146 of QRS complex 120 in the illustrated example. As can be seen in FIG. 4, QRS width 148 represents the width of the overall depolarization of ventricles 18 and 22.

DSP 100 may identify beginning points 134-138 and ending points 140-144 as threshold-crossings of the digital signal or zero-crossings of the first derivative of the digital signal.

DSP 100 may measure amplitudes of R-waves as maximum or minimum values of the digital signal depending on the polarity of the signal. The accuracy of the correlation between beginning points 134-138, ending points 140-144, and the amplitudes on one hand, and the actual beginning and end of QRS complexes 116-120 and amplitudes on the other is not critical because, as will be described below, multiple measurements are considered by microprocessor 60 in assessing left ventricular function. Nonetheless, use of DSP 100 allows for accurate measurement of the values within each cardiac cycle, and, importantly, consistent measurement of these values from cycle-to-cycle. DSP 100 may be more resistant to noise within signals 110-114 and system noise than existing analog components capable of measuring these values.

Figure 5:
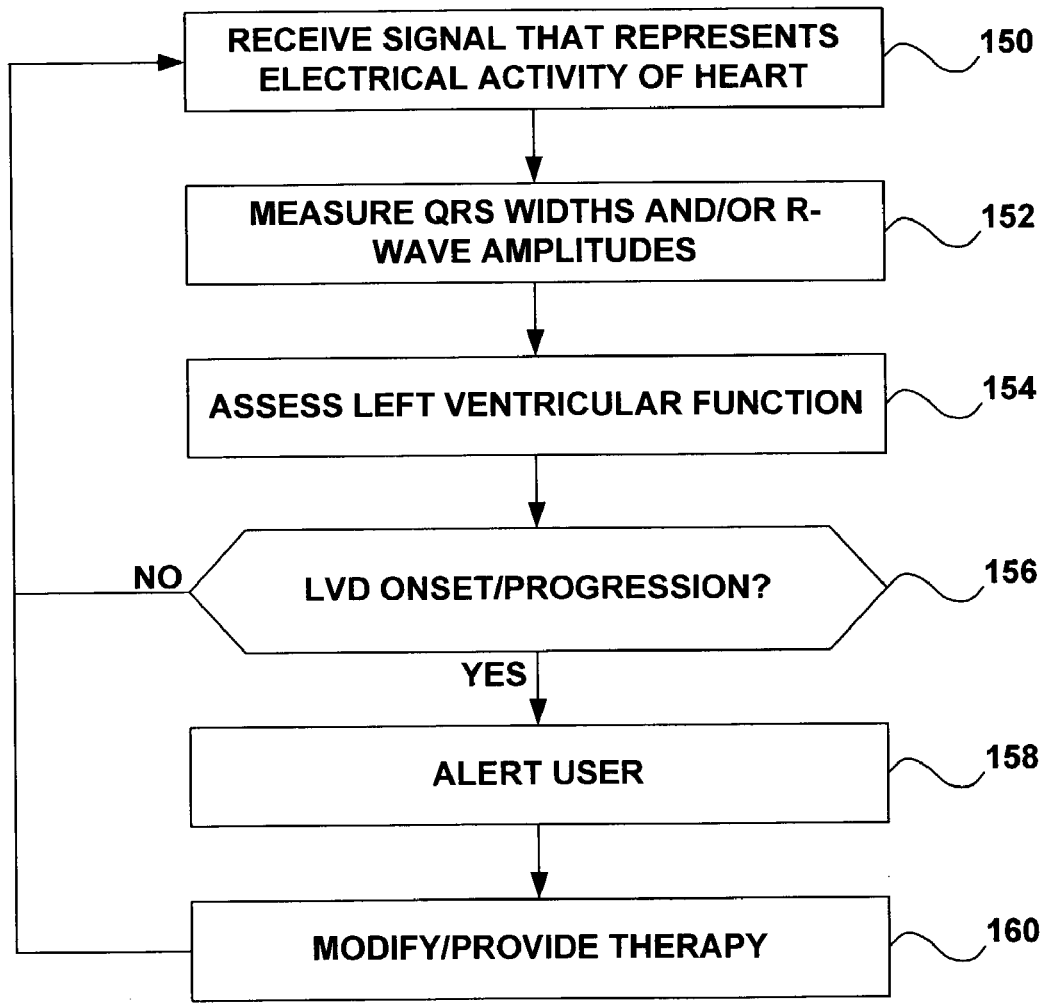
FIG. 5 is a flow diagram illustrating an example method that may be employed by the implantable medical device of FIG. 1 to identify left ventricular dysfunction.

FIG. 5 is a flow diagram illustrating an example method that may be employed by IMD 10 to identify LVD. IMD 10 receives one or more signals that represent electrical activity of heart 16 by any of the techniques described above (150). The signals are converted to one or more digital signals by A/D converter 98, and DSP 100 processes the digital signals to measure widths of QRS complexes and/or amplitudes of R-waves within the signals (152). Where two or more signals are processed, DSP 100 or microprocessor 60 may determine average values or weighted average values for each cardiac cycle based on the values for each signal.

Microprocessor 60 assesses left ventricular function based on the measured values (154), and determines whether the measurements indicate onset or progression of LVD (156), as will be described in greater detail below with reference to FIG. 6. As discussed above, microprocessor 60 may alert a user (158) based on the determination. For example, microprocessor 60 may activate patient alarm 104, or provide an indication via telemetry circuit 106, as described above. Further microprocessor may initiate or modify therapy (160), as described above.

Figure 6:
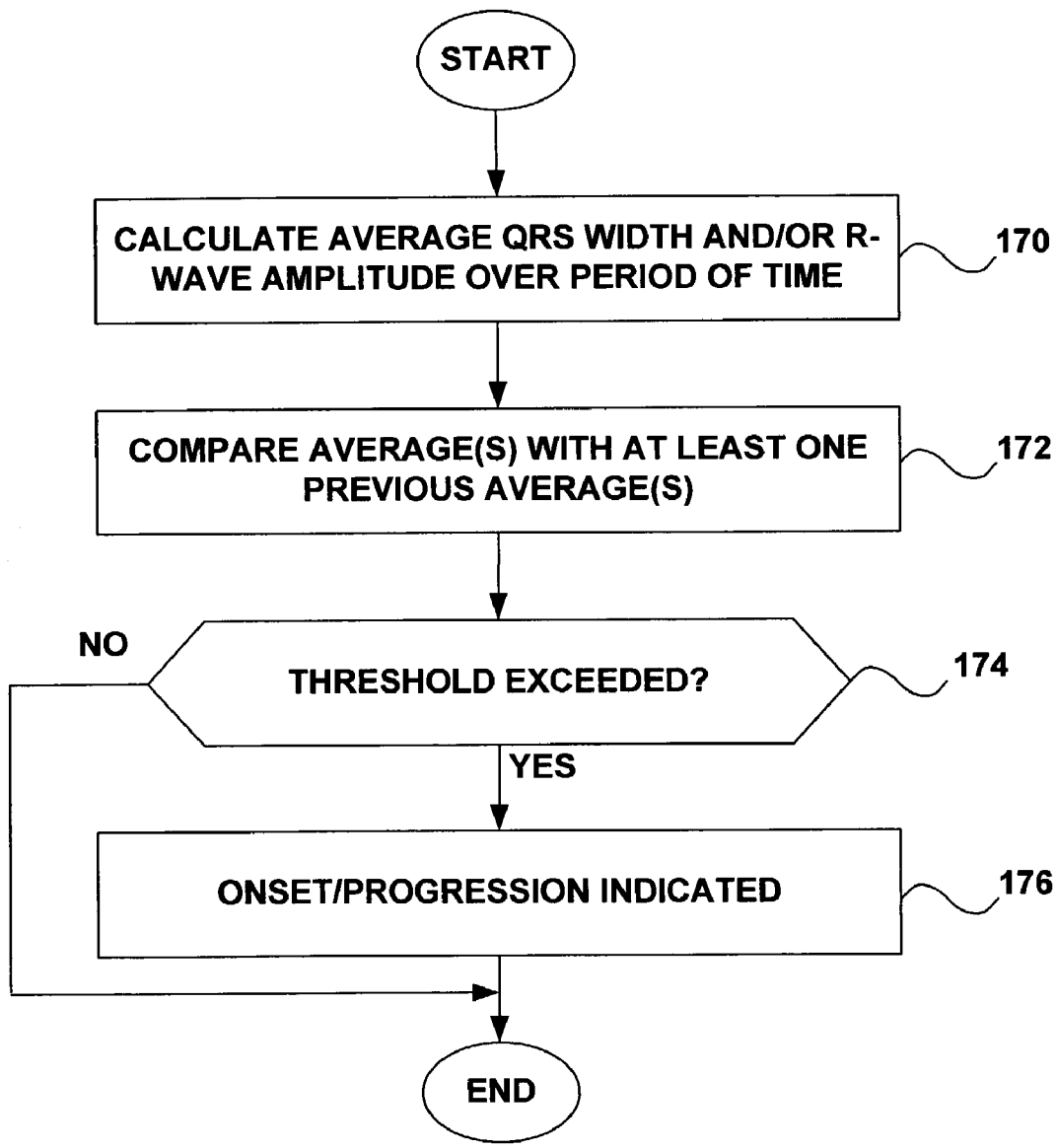
FIG. 6 is a flow diagram illustrating the method of FIG. 5 in greater detail according to an embodiment of the invention.

FIG. 6 is a flow diagram illustrating the method of FIG. 5 in greater detail according to an embodiment of the invention. In particular, FIG. 6 illustrates an example method that may be employed by IMD 10 to identify onset or progression of LVD. In the illustrated example, microprocessor 60 assesses trends in QRS widths and/or R-wave amplitudes measured by DSP 100, and identifies onset or progression of LVD based on the trends. For example, microprocessor 60 may identify increases in the QRS width over time or decreases in R-wave amplitude over time.

According to the illustrated example, microprocessor 60 calculates an average of QRS widths and/or R-wave amplitudes measured during periods of time (170). The periods of time may, for example, be one or more days, weeks, or months. The average value calculated during a first period may be a baseline value. Microprocessor 60 may compare average values calculated during subsequent periods to the baseline value, or any previously determined average value or combination of previously determined average values (172).

The comparison may, for example, involve determining an absolute difference between the average values for two time periods, a percentage difference between the average values for two time periods, or the rate of change over two or more time periods. The difference, percentage, or rate may be compared to a threshold value, and if the threshold is exceeded (174) microprocessor 60 may identify onset or progression of LVD as having occurred (176). For example, an increase in QRS width or decrease in R-wave amplitude between five and ten percent over a period of several months may be indicative of LVD onset or progression, and the threshold may be set accordingly.

On a beat-to-beat, hour-to-hour, or even day-to-day basis, QRS widths and R-wave amplitudes may vary substantially. This variation may, for example, be based on varying activity of patient 12. IMD 10 may be able to more accurately identify onset or progression of LVD by identifying onset or progression based on trends in the measured QRS widths and/or R-wave amplitudes, thus avoiding detection based on short-term fluctuations. Further, absolute QRS widths and R-wave amplitudes may vary from patient-to-patient. By measuring baseline values and assessing trends, IMD 10 may more easily account for patient-to-patient variation in such measurements.

A clinician may program a variety of parameters associated with the detection of and response to LVD via a programming device in order to address differences between patients. For example, the clinician may adjust parameters depending on the perceived likelihood that patient 12 will develop LVD, or whether the patient has already developed LVD and progression is being monitored. The clinician may adjust the period over which an average value is calculated and the threshold value or values. The clinician may also program the response of IMD 10, e.g., indication or therapy control, to account for patient-to-patient differences.

Figure 7:
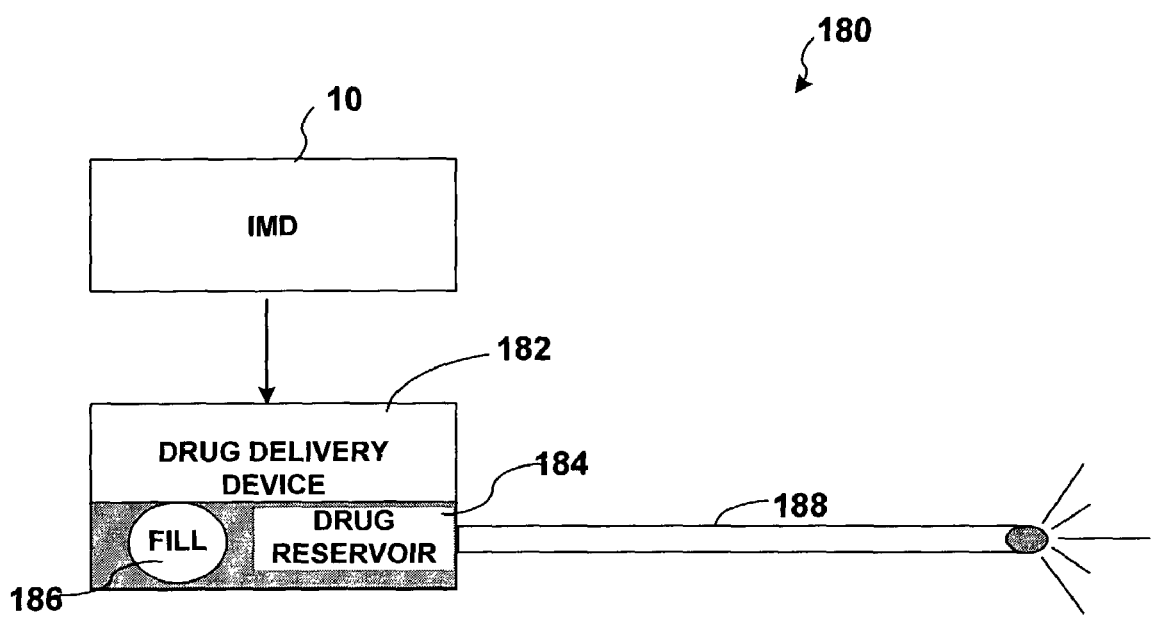
FIG. 7 is a block diagram illustrating an example system including the implantable medical device of FIG. 1 and an implantable drug delivery device.

FIG. 7 is a block diagram illustrating an example system 180 including IMD 10 and an implantable drug delivery device 182. IMD 10 may control delivery of one or more drugs by drug delivery device 182 based on identification of onset or progression of LVD. Drug delivery device 182 may be an implantable drug pump, such as one of the SynchroMed™ pumps manufactured by and commercially available from Medtronic Inc. of Minneapolis, Minn.

Drug delivery device 182 may include one or more reservoirs that contain a drug or mixture of drugs. The drug or drugs may include drugs used to treat left ventricular dysfunctions, such as beta-blockers, ACE inhibitors, or inotropic drugs. In FIG. 7, drug delivery device 182 is shown with a single reservoir 184. Drug delivery device 182 may further include a fill port 186 to assist filling or refilling of reservoir 184.

Drug delivery device 182 may include one or more infusion apparatuses, such as catheter 188 that infuses a drug from reservoir 184 to infusion sites within patient 12. Drug delivery device 182 also may include one or more pumps (not shown) that deliver the drug from reservoir 184 to catheter 188. The infusion site may depend upon the drug being infused, and may be the subclavian vein, superior vena cava, or fatty tissue of patient 12. The drugs being delivered may be delivered by a constant drip, a periodic bolus, a combination of these methods, or some other delivery method. The present invention is not limited to a particular drug or drug delivery method.

IMD 10 controls drug delivery device 182 to begin delivering a drug upon identifying onset or progression of LVD, or may control drug delivery device 182 to adjust a dosage of a drug based on the identification. In some embodiments, IMD 10 may simply indicate LVD to drug delivery device 182, and drug delivery device 182 may determine whether to initiate drug delivery or modify drug deliver, and what an appropriate dosage should be, based on the indication. In some embodiments, IMD 10 and drug delivery device 182 may be embodied within a single implantable medical device, for example a drug delivery device additionally capable of detecting LVD.

A number of embodiments of the invention have been described. However, one skilled in the art will appreciate that the invention can be practiced with embodiments other than those disclosed. The disclosed embodiments are presented for purposes of illustration and not limitation, and the invention is limited only by the claims that follow.

What is claimed is:

1. A device comprising:
   a first implantable electrode pair configured to detect a first signal that represents right ventricular cardiac activity;
   a second implantable electrode pair configured to detect a second signal that represents left ventricular cardiac activity; and
   a processor to digitally process the first and second signals to measure a value of a characteristic of each of a plurality of QRS complexes within the first and second signals and indicate left ventricular dysfunction responsive to differences between the measured values for the QRS complexes wherein the measured values are intervals each beginning at a first time when a said QRS complex begins in one of the first and second signals and ending at a second time when the said QRS complex ends in the other of the first and second signals.

2. The device of claim 1, wherein the processor digitally processes the first and second signals to measure a width of each of the QRS complexes.

3. The device of claim 1, wherein the processor further digitally processes the first and second signals to measure an amplitude of each of a plurality of R-waves within each of the plurality of QRS complexes.

4. The device of claim 1, wherein the processor identifies a trend within the measured values for the QRS complexes, and indicates left ventricular dysfunction based on the trend.

5. The device of claim 1, wherein the processor determines a first average measured value for a first subset of the QRS complexes and a second average measured value for a second subset of the QRS complexes, compares the first and second average values, and indicates left ventricular dysfunction to the user based on the comparison.

6. The device of claim 5, wherein the processor determines a percent change from the first average value to the second average value, and compares the percent change to a threshold value.

7. The device of claim 1, further comprising a patient alarm, wherein the processor indicates left ventricular dysfunction to the user by activating the patient alarm.

8. The device of claim 1, further comprising:
   a memory; and
   a telemetry circuit operable coupled with the processor to facilitate external data communication that includes an indication of left ventricular dysfunction.

9. The device of claim 1, further comprising means for delivering therapy controlled by the processor based on the measured values.

10. The device of claim 9, wherein the device is a multi-chamber pacemaker and the means for delivering therapy include a cardiac resynchronization therapy.

11. The device of claim 9, wherein the device is a rate-responsive pacemaker, and the processor adjusts aggressiveness of rate-responsive pacing based on the measured values.

12. The device of claim 1, wherein the processor comprises a digital signal processor to digitally process the first and second signals and a microprocessor to indicate left ventricular dysfunction to the user.

13. The device of claim 1, further comprising a housing forming a can electrode that is utilized as one portion of the first or second electrode pairs.

14. The device of claim 1, wherein the processor indicates at least one of onset and progression of left ventricular dysfunction.

15. A method for assessing cardiac function comprising:
   receiving a first signal that represents electrical activity within a right ventricle of the heart via a first electrode pair;
   receiving a second signal that represents electrical activity within a left ventricle of the heart via a second electrode pair;
   digitally processing the first and second signals to measure a value of a characteristic for each of a plurality of QRS complexes within the first and second signals wherein the measured values are intervals beginning at a first time when a said QRS complex begins in one of the first and second signals and ending at a second time when the said QRS complex ends in the other of the first and second signals; and
   indicating left ventricular dysfunction responsive to differences between the measured values for the QRS complexes.

16. The method of claim 15, wherein digitally processing the first and second signals comprises digitally processing the first and second signals to measure a width of each of the QRS complexes.

17. The method of claim 15, wherein digitally processing the first and second signals further comprises digitally processing the first and second signals to measure an amplitude of each of a plurality of R-waves within each of the plurality of QRS complexes.

18. The method of claim 15, further comprising identifying a trend within the measured values for the QRS complexes, wherein indicating left ventricular dysfunction to a user comprises indicating left ventricular dysfunction based on the trend.

19. The method of claim 15, further comprising:
   determining a first average measured value for a first subset of the QRS complexes and a second average measured value for a second subset of the QRS complexes; and
   comparing the first and second average values, and wherein indicating left ventricular dysfunction to a user comprises indicating left ventricular dysfunction to the user based on the comparison.

20. The method of claim 19, wherein comparing the first and second average values comprises:
   determining a percent change from the first average value to the second average value; and
   comparing the percent change to a threshold value.

21. The method of claim 15, wherein indicating left ventricular dysfunction to a user comprises activating a patient alarm.

22. The method of claim 15, wherein indicating left ventricular dysfunctions to a user comprises:
   storing an indication of left ventricular dysfunction within a memory; and
   providing the indication to the user via a programming device upon interrogation by the programming device.

23. The method of claim 15, further comprising controlling delivery of therapy to the patient based on the measured values.

24. The method of claim 23, wherein controlling delivery of therapy comprises controlling delivery of a drug by an implanted drug delivery device.

25. The method of claim 23, wherein controlling delivery of therapy comprises controlling delivery of cardiac resynchronization pacing.

26. The method of claim 23, wherein controlling delivery of therapy comprises adjusting aggressiveness of rate-responsive pacing.

27. The method of claim 15, wherein indicating left ventricular dysfunction comprises indicating at least one of onset and progression of left ventricular dysfunction.

* * * * *